(12) United States Patent
Lee et al.

(10) Patent No.: US 11,957,706 B2
(45) Date of Patent: Apr. 16, 2024

(54) COMPOSITION FOR PREVENTING OR TREATING FIBROSIS INCLUDING AN INHIBITOR OF CDK17 EXPRESSION OR ACTIVITY

(71) Applicant: KOREA UNIVERSITY RESEARCH AND BUSINESS FOUNDATION, Seoul (KR)

(72) Inventors: Young Sik Lee, Seoul (KR); Do Hoon Lee, Seoul (KR); Min Seok Choi, Seoul (KR); Jae Sang Hong, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 0 days.

(21) Appl. No.: 17/828,351

(22) Filed: May 31, 2022

(65) Prior Publication Data

US 2022/0387473 A1    Dec. 8, 2022

(30) Foreign Application Priority Data

Jun. 3, 2021  (KR) .................. 10-2021-0072162
May 20, 2022  (KR) .................. 10-2022-0062069

(51) Int. Cl.

| | |
|---|---|
| *C12N 15/11* | (2006.01) |
| *A23L 33/13* | (2016.01) |
| *A61K 31/713* | (2006.01) |
| *C12N 15/113* | (2010.01) |

(52) U.S. Cl.
CPC ............ *A61K 31/713* (2013.01); *A23L 33/13* (2016.08); *C12N 15/11* (2013.01); *C12N 15/1137* (2013.01)

(58) Field of Classification Search
CPC .......................... A61K 31/713; C12N 15/1137
See application file for complete search history.

(56) References Cited

PUBLICATIONS

Todd, Nevins W., Irina G. Luzina, and Sergel P. Atamas. "Molecular and cellular mechanisms of pulmonary fibrosis." *Fibrogenesis & tissue repair* 5.1 (Jul. 23, 2012): pp. 1-24.
Li, Dan, and Scott Friedman. "Liver fibrogenesis and the role of hepatic stellate cells: new insights and prospects for therapy." *Journal of gastroenterology and hepatology* 14.7 (Feb. 19, 1999): pp. 618-633.
Gross, Thomas J., and Gary W. Hunninghake. "Idiopathic pulmonary fibrosis." *New England Journal of Medicine* 345.7 (Aug. 16, 2001): pp. 517-525.

*Primary Examiner* — Ekaterina Poliakova-Georgantas
(74) *Attorney, Agent, or Firm* — NSIP Law

(57) ABSTRACT

The present disclosure relates to a composition for preventing or treating fibrosis including an inhibitor of cyclin-dependent kinase 17 (CDK17) expression or activity. According to the present disclosure, the inhibitor of CDK17 expression or activity significantly reduces collagen production and cell activity and viability in activated hepatic stellate cells (liver fibrosis cell model), renal tubular epithelial cells (renal fibrosis cell model) in which fibrosis is induced by TGF-β treatment, and alveolar epithelial cells (lung fibrosis cell model) in which fibrosis is induced by TGF-β treatment, indicating that the composition of the present disclosure has an excellent effect in preventing or treating fibrosis.

4 Claims, 6 Drawing Sheets
Specification includes a Sequence Listing.

[FIG. 1]
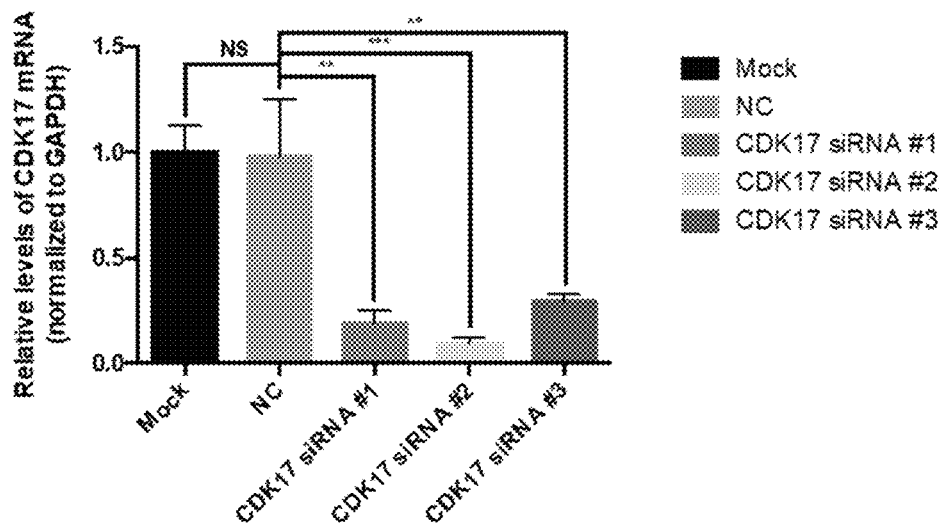
[FIG. 2]
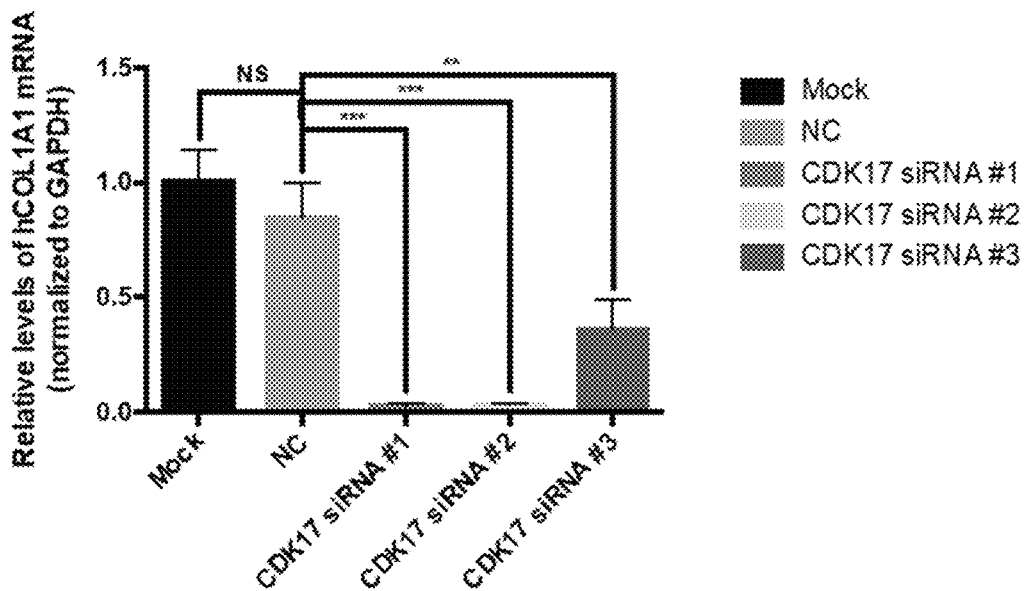

[FIG. 3]
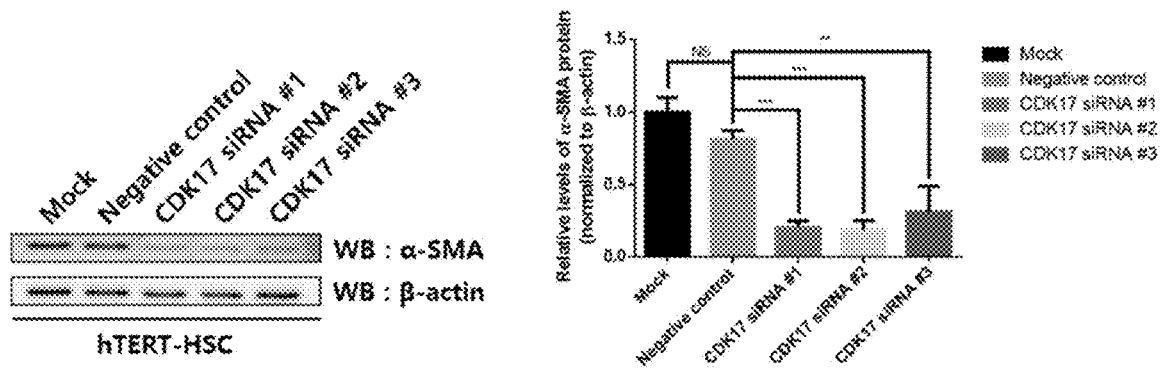
[FIG. 4]
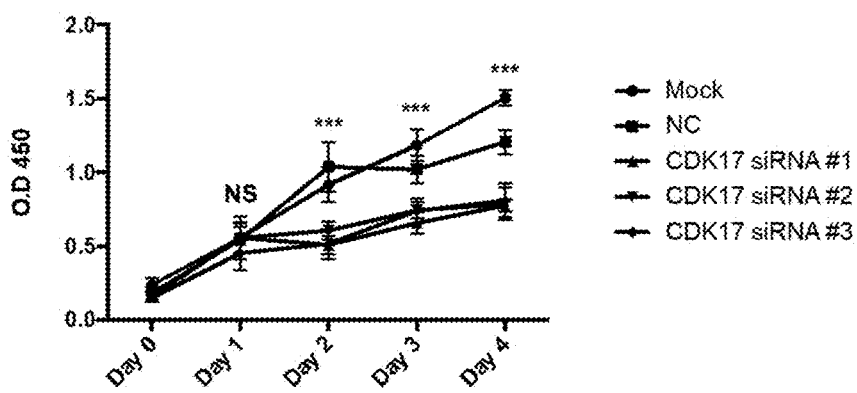

[FIG. 5]
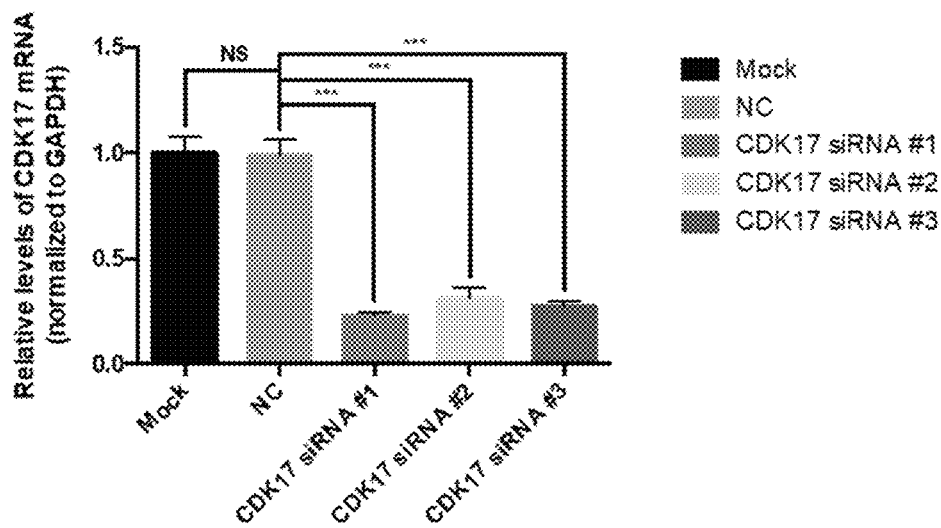
[FIG. 6]
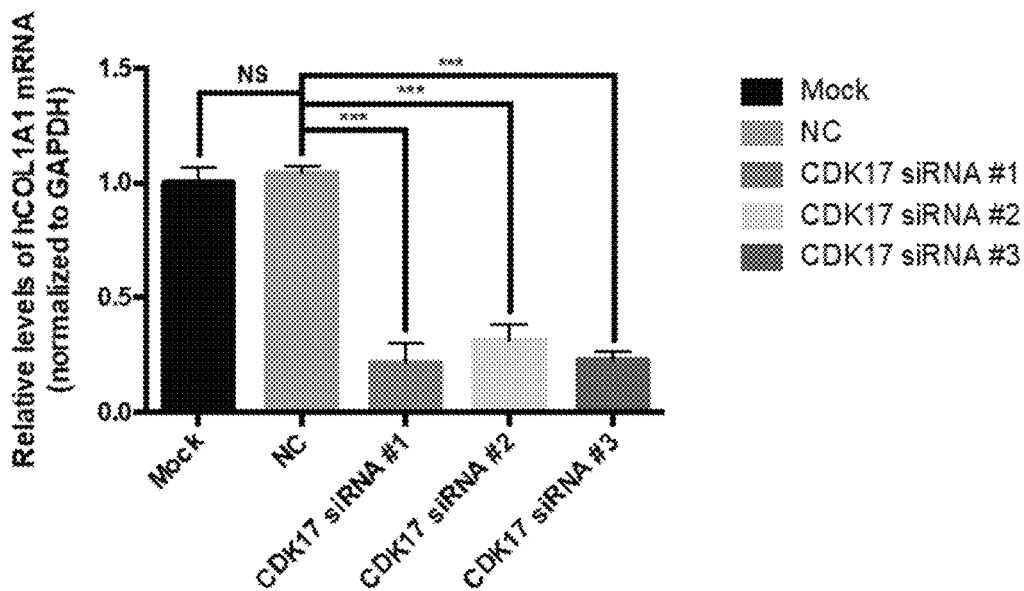

[FIG. 7]
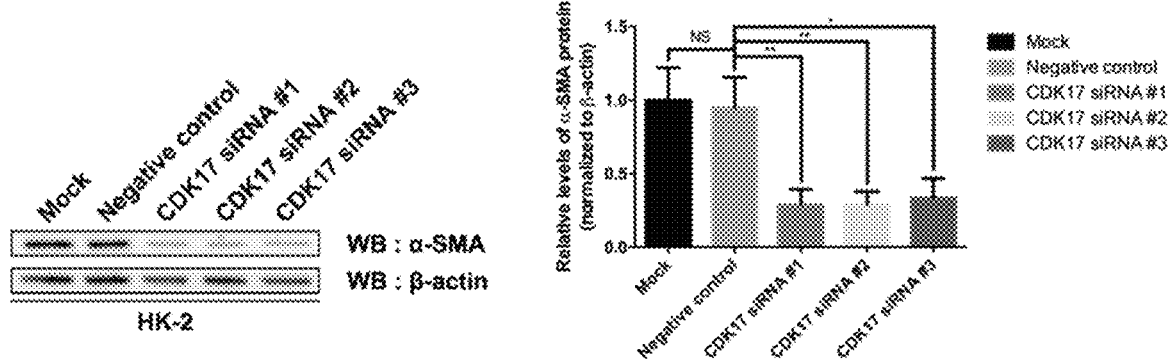
[FIG. 8]
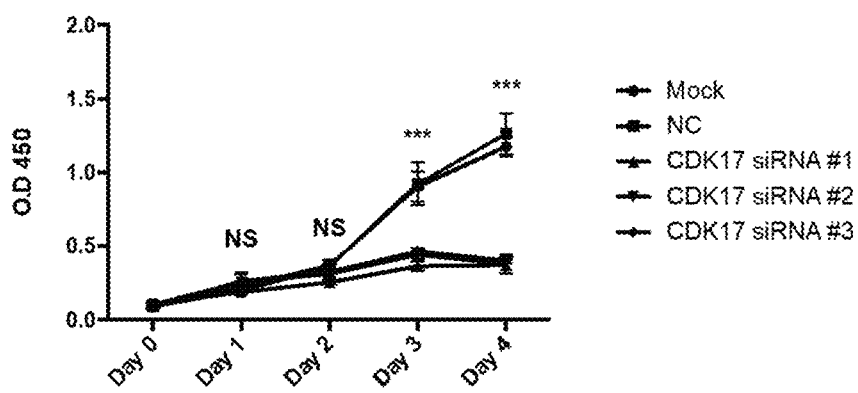

[FIG. 9]
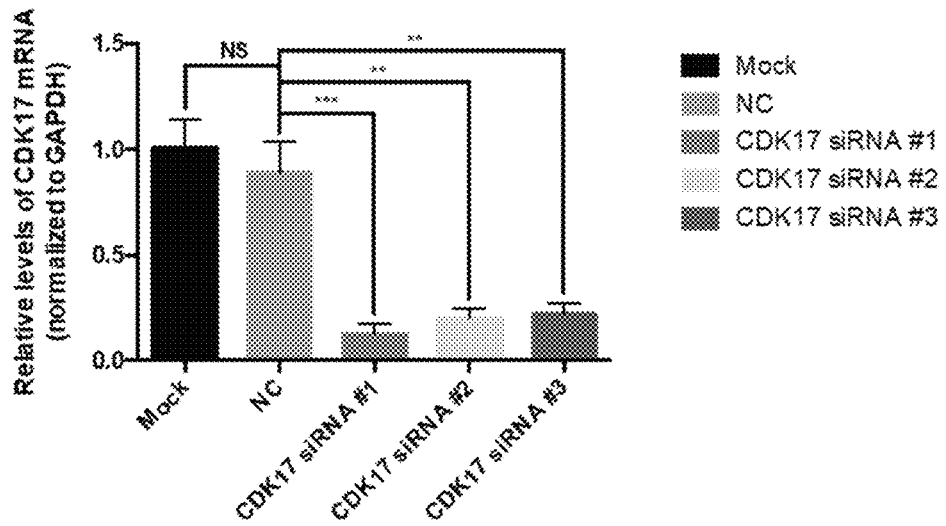
[FIG. 10]
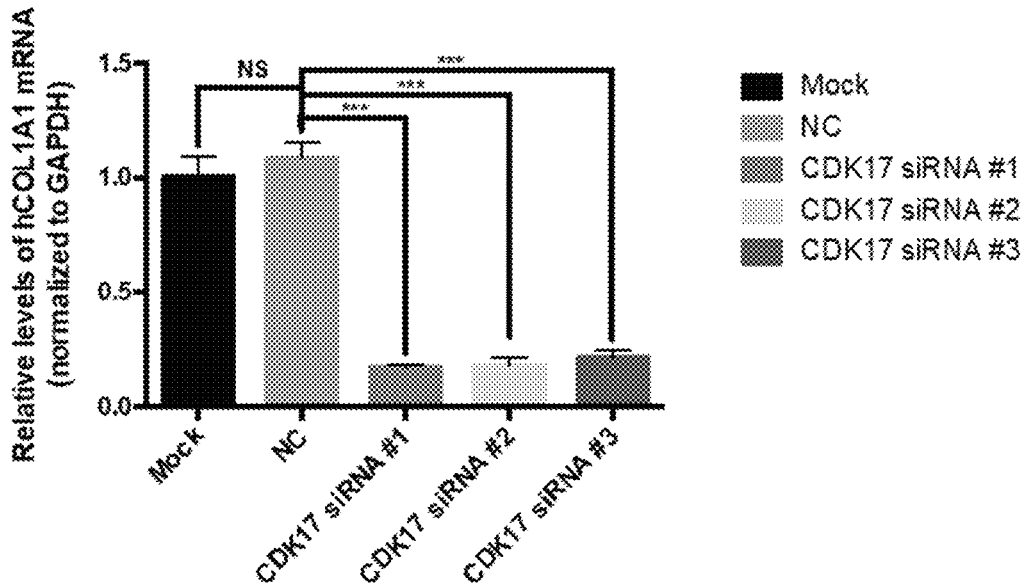

[FIG. 11]
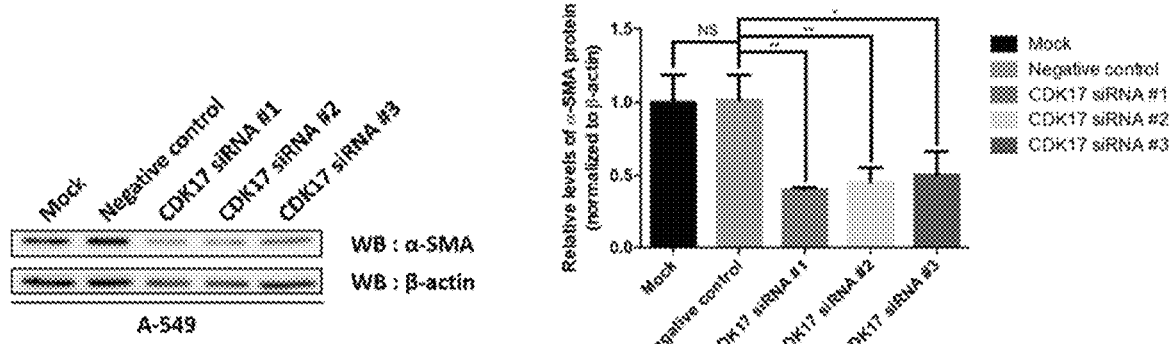
[FIG. 12]
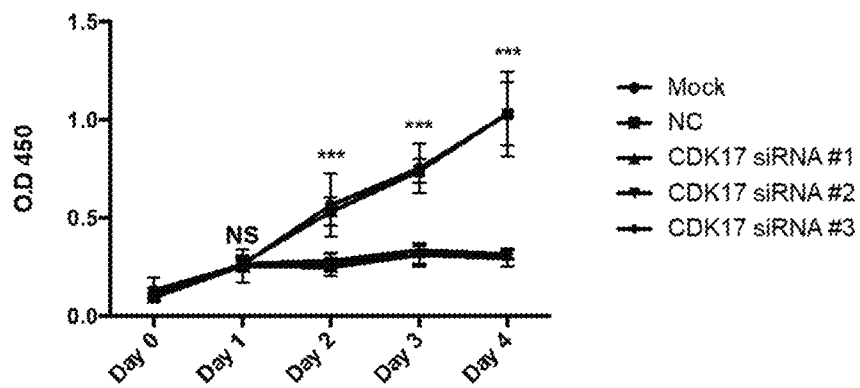

```
                         SEQUENCE LISTING

<160> NUMBER OF SEQ ID NOS: 6

<210> SEQ ID NO 1
   <211> LENGTH: 19
   <212> TYPE: RNA
   <213> ORGANISM: Artificial Sequence
   <220> FEATURE:
   <223> OTHER INFORMATION: Human CDK17 siRNA #1 sense

<400> SEQUENCE: 1
guccucuuca caguggagu                                              19

<210> SEQ ID NO 2
   <211> LENGTH: 19
   <212> TYPE: RNA
   <213> ORGANISM: Artificial Sequence
   <220> FEATURE:
   <223> OTHER INFORMATION: Human CDK17 siRNA #1 antisense

<400> SEQUENCE: 2
acuccacugu gaagaggac                                              19

<210> SEQ ID NO 3
   <211> LENGTH: 19
   <212> TYPE: RNA
   <213> ORGANISM: Artificial Sequence
   <220> FEATURE:
   <223> OTHER INFORMATION: Human CDK17 siRNA #2 sense

<400> SEQUENCE: 3
cuaacaaacu gcuguucuu                                              19

<210> SEQ ID NO 4
   <211> LENGTH: 19
   <212> TYPE: RNA
   <213> ORGANISM: Artificial Sequence
   <220> FEATURE:
   <223> OTHER INFORMATION: Human CDK17 siRNA #2 antisense

<400> SEQUENCE: 4
aagaacagca guuuguuag                                              19

<210> SEQ ID NO 5
   <211> LENGTH: 19
   <212> TYPE: RNA
   <213> ORGANISM: Artificial Sequence
   <220> FEATURE:
   <223> OTHER INFORMATION: Human CDK17 siRNA #3 sense
```

```
<400> SEQUENCE: 5
caguacacag gaucuuuca                                                 19

<210> SEQ ID NO 6
<211> LENGTH: 19
<212> TYPE: RNA
<213> ORGANISM: Artificial Sequence
<220> FEATURE:
<223> OTHER INFORMATION: Human CDK17 siRNA #3 antisense

<400> SEQUENCE: 6
ugaaagaucc uguguacug                                                 19
```

COMPOSITION FOR PREVENTING OR TREATING FIBROSIS INCLUDING AN INHIBITOR OF CDK17 EXPRESSION OR ACTIVITY

CROSS-REFERENCE TO RELATED APPLICATION

This application claims priority to Korean Patent Application Nos. 10-2021-0072162, filed on Jun. 3, 2021 and 10-2022-0062069, filed on May 20, 2022, in the Korean Intellectual Property Office, the disclosures of which are incorporated herein by reference.

BACKGROUND OF THE DISCLOSURE

Field of the Disclosure

The present disclosure relates to a composition for preventing or treating fibrosis including an inhibitor of cyclin-dependent kinase 17 (CDK17) expression or activity.

Description of the Related Art

Fibrosis is a disease resulting from abnormal production, accumulation, and deposition of extracellular matrix by fibroblasts, i.e., caused by fibrosis of an organ or tissue. Fibrosis is a very fatal disease that causes organ damage. Tissue fibrosis is commonly found in various diseases such as liver fibrosis, cirrhosis, chronic pancreatitis, renal failure, and lung fibrosis (pulmonary sclerosis).

For example, when inflammatory reaction continues due to damage to the liver tissues, as liver fibrosis occurs, a large amount of collagen secreted by active hepatic stellate cells (HSCs) is combined with the extracellular matrix (ECM). That is, liver fibrosis is a process for wound healing. When liver fibrosis continues, a large amount of collagen is deposited in the liver tissues, regenerated nodules are surrounded by collagen, and liver cirrhosis with an abnormal structure occurs (LIVER FIBROGENESIS AND THE ROLE OF HEPATIC STELLATE CELLS: NEW INSIGHTS AND PROSPECTS FOR THERAPY, J Gastroenterol Hepatol. 14, 618-633).

As another example, idiopathic lung fibrosis (IPF) occurs because of recurrent injury of alveolar epithelial cells associated with accumulation of fibroblasts and differentiation of myofibroblasts. IPF is a chronic, progressive, and lethal disease that causes irreversible destruction of the lung parenchyma tissues and excessive accumulation of extracellular matrix (ECM). However, until now, since there is no effective treatment for fibrosis (MOLECULAR AND CELLULAR MECHANISMS OF PULMONARY FIBROSIS, Fibrogenesis Tissue Repair, 2012, 5(1): 11; IDIOPATHIC PULMONARY FIBROSIS, N Engl J Med, 2001, 345(7): 517-25), development of a prophylactic/therapeutic agent capable of effectively preventing or treating fibrosis is continuously required.

RNA interference (RNAi) is a process of regulating expression of a target gene by small interfering RNA (siRNA) or microRNA (miRNA), which is a protein non-coding ribonucleic acid (RNA) consisting of about 22 nucleotides. Specifically, in RNAi-mediated gene expression regulation, mRNA complementary to siRNA or miRNA is degraded or translation of the mRNA is inhibited. RNAi is closely related to almost all biological processes such as development and physiology of a living organism, cell differentiation, proliferation, and death, and stability of genomes. In addition, RNAi is closely associated with resistance to viruses and various human diseases.

Since RNAi can be used to regulate genes associated with diseases, RNAi is important in medicine. In particular, since high specificity and high efficiency for a specific gene can be secured even with a small amount of siRNA, development of siRNA-based therapeutics is progressing worldwide.

Accordingly, due to limitless potential of RNAi in basic fields and pharmaceutical application fields, the market size for RNAi technology continues to grow. According to Frost & Sullivan research, the global market for RNAi technology has increased dramatically from 48 million (2003) to 328 million (2010). Also, according to a report released by BBC Research, the market for RNAi technology is expected to grow to 3.6 billion in 2013, with a compound annual growth rate (CAGR) of 83.4%. In addition, according to Jain PharmaBioTech research, the market size of new drug development based on RNAi technology doubled from 500 million in 2004 to 1 billion in 2010. According to another study, the market size of RNAi-based therapy is expected to reach 2.3 billion in 2013.

Accordingly, based on these studies, there is a need for a new treatment method that can significantly change the existing limited treatment method through verification of fibrosis recovery.

SUMMARY OF THE DISCLOSURE

As a result of efforts to develop a composition for preventing or treating fibrosis, the present inventors confirmed a novel role of CDK17 and the effectiveness of an inhibitor of CDK17 expression or activity in preventing and treating fibrosis. Based on these results, the present inventors conducted further studies to complete the present disclosure.

Therefore, the present disclosure has been made in view of the above problems, and it is an object of the present disclosure to provide a pharmaceutical composition for preventing or treating fibrosis including an inhibitor of CDK17 expression or activity.

It is another object of the present disclosure to provide a method of preventing or treating fibrosis including a step of administering to a subject an inhibitor of CDK17 expression or activity, or a composition including the inhibitor of CDK17 expression or activity.

It is yet another object of the present disclosure to provide a health functional food for preventing or alleviating fibrosis including an inhibitor of CDK17 expression or activity.

Hereinafter, the present disclosure will be described in detail.

However, the disclosure may be embodied in many different forms and should not be construed as being limited to the embodiments set forth herein. These embodiments are provided to more fully describe the present disclosure to those skilled in the art. In the present disclosure, it is to be understood that, unless stated otherwise, when a part "comprises" any element, the part may include other elements without excluding other elements.

The present disclosure relates to a pharmaceutical composition for preventing or treating fibrosis including an inhibitor of CDK17 expression or activity.

In the present disclosure, "cyclin-dependent kinase 17 (CDK17)" is a protein-coding gene, and CDK17-related diseases include posterior amorphous corneal dystrophy. According to gene ontology (GO) annotations associated with this gene, CDK17 protein has transferase activity, phosphorus-containing group transfer activity, and protein tyrosine kinase activity. In addition, CDK17 protein has serine/threonine kinase activity against histone H1 protein.

In the present disclosure, "inhibitor of CDK17 expression or activity" refers to a substance that reduces the expression or activity of CDK17 gene in a cell. Specifically, the inhibitor refers to a substance that reduces the expression level of CDK17 gene or the activity of CDK17 protein. More specifically, the inhibitor acts directly on CDK17 gene or indirectly acts on an upstream regulator of CDK17 gene to decrease expression of CDK17 gene at transcriptional level or promotes degradation of expressed CDK17 gene or interferes with the activity thereof. Specifically, an inhibitor of CDK17 expression or activity includes one or more selected from the group consisting of antisense nucleotides complementary to CDK17 mRNA, ribonucleic acids such as small hairpin RNA (shRNA), small interfering RNA (siRNA), and microRNA (miRNA), and ribozymes, without being limited thereto.

In the present disclosure, "ribonucleic acid" may include small RNA. "Small RNA" is a short-length RNA with 200 or less nucleotide sequences, and "small RNA" is not translated into a protein and promotes degradation of a specific mRNA or inhibits translation of a specific mRNA through complementary binding. Small RNAs include small interfering RNAs (siRNAs), microRNAs (miRNAs), piwi-associated RNAs (piRNAs), and long non-coding RNAs.

In the present disclosure, "small interfering RNA (siRNA)" refers to a protein non-coding RNA consisting of 21 to 23 nucleotides capable of inducing RNA interference (RNAi) through cleavage and degradation of a specific mRNA. siRNA includes a sense RNA strand having a sequence homologous to mRNA of a target gene and an antisense RNA strand having a complementary sequence thereto. Since siRNA may inhibit expression of a target gene, siRNA is used in a gene knockdown method or a gene therapy method.

In the present disclosure, "short hairpin RNA (shRNA)" is a single-stranded RNA and is divided into a stem portion forming a double-stranded portion by hydrogen bonding and a loop portion having a ring shape. "Short hairpin RNA (shRNA)" may be processed by a protein such as Dicer to be converted into siRNA and perform the same function as siRNA.

In the present disclosure, "microRNA (miRNA)" refers to a protein non-coding RNA consisting of 21 to 23 nucleotides that regulates expression of a sequence complementary gene after transcription by promoting degradation of a target mRNA or inhibiting translation thereof.

In the present disclosure, "ribozyme" refers to an RNA molecule having an enzyme-like function to recognize a specific nucleotide sequence and cut the nucleotide sequence. A ribozyme is a complementary nucleotide sequence of a target mRNA strand and consists of a region that binds with specificity and a region that cuts a target mRNA.

In the present disclosure, "fibrosis" means formation of an excess of fibrous connective sites in an organ or tissue. This site may be distinguished from a fibrous site as a normal component in an organ or tissue. Due to excessive accumulation of an extracellular matrix such as fibronectin and collagen by fibroblasts, fibrosis may be understood as a fatal disease that ultimately causes organ damage.

In the present disclosure, fibrosis may occur in lungs, kidneys, a liver, a heart, a brain, blood vessels, joints, intestines, skin, soft tissues, bone marrow, a penis, a peritoneum, muscles, a spine, testes, ovaries, breasts, a thyroid, tympanic membranes, a pancreas, a gallbladder, a bladder, or a prostate. In the present disclosure, fibrosis may be a disease caused by fibrosis occurring in each tissue of the body. For example, fibrosis may be abnormal wound healing, liver fibrosis, connective fibrosis, Crohn's disease (fibrosis of the intestine), cystic fibrosis of the pancreas and lungs, injection fibrosis, which may occur as a complication of intramuscular injection, especially in children, endocardial myocardial fibrosis or cardiac fibrosis, fibrosis by graft-versus-host disease (GVHD), spleen fibrosis, eye fibrosis including retinal fibrosis, fibrotic complications of surgical or injection fibrosis, glomerulonephritis, interstitial fibrosis, keloid and hypertrophic scarring (skin fibrosis), macular degeneration, mediastinal fibrosis (soft tissue fibrosis of the mediastinum), focal scleroderma (morphea), multifocal fibrosis, myelofibrosis, renal systemic fibrosis, nodular epidermal fibrosis (e.g., benign fibrous histiocytoma, pleural fibrosis), fibrosis as a result of surgery (e.g., surgical transplantation), proliferative fibrosis, pipestem fibrosis, post-fibrinous fibrosis, progressive multiple fibrosis (a type of lung fibrosis, a complication of coal workers' pneumoconiosis), old myocardial infarction (heart fibrosis), pancreatic fibrosis, progressive multiple fibrosis, radiation fibrosis, renal fibrosis, renal fibrosis associated with or causing chronic kidney disease, retroperitoneal fibrosis (fibrosis of the soft tissues of the retroperitoneum), post-surgical scarring, scleroderma/systemic sclerosis (skin fibrosis), epithelial cytosis, uterine fibrosis, or viral hepatitis-induced fibrosis, without being limited thereto.

In the present disclosure, "liver fibrosis" refers to a process of wound healing that appears through combination of collagen and extracellular matrix (ECM) secreted in large amounts from activated hepatic stellate cells as an inflammatory response continues due to damage to the liver tissue. When liver fibrosis continues, a large amount of collagen is deposited in the liver tissue, regenerative nodules are surrounded by collagen, and liver fibrosis may develop into cirrhosis, which has an abnormal structure.

In the present disclosure, the term "prevention" refers to any act of preventing occurrence of a desired symptom or disease by administering the composition of the present disclosure, or delaying occurrence or expression thereof.

In the present disclosure, the term "treatment" refers to any action that improves or eliminates a desired symptom or disease by administering the composition of the present disclosure.

Meanwhile, the composition of the present disclosure may further include a pharmaceutically acceptable carrier, and the composition may be formulated in combination with the carrier.

In the present disclosure, the term "pharmaceutically acceptable carrier" refers to a carrier or diluent that does not irritate organisms and does not impair the biological activity and properties of an administered compound. Examples of acceptable pharmaceutical carriers for compositions formulated as liquid solutions are sterile and biocompatible, and include saline, sterile water, Ringer's solution, buffered saline, albumin injection, dextrose solution, maltodextrin solution, glycerol, ethanol, and a mixture containing one or more of the components, and other conventional additives such as antioxidants, buffers, and bacteriostats may be added as needed. In addition, diluents, dispersants, surfactants, binders and lubricants may be additionally added to form an injectable formulation such as an aqueous solution, suspension, emulsion, etc., pills, capsules, granules or tablets.

The composition of the present disclosure may be applied to any formulation containing the composition of the present disclosure or the inhibitor of CDK17 expression or activity as an active ingredient, may be prepared in oral or parenteral formulations, and may be formulated in a unit dosage form for ease of administration and uniformity of dosage. The pharmaceutical formulation of the present disclosure includes oral, rectal, nasal, topical (including buccal and sublingual), subcutaneous, vaginal or parenteral (including intramuscular, subcutaneous, and intravenous), and forms suitable for administration, inhalation, or insufflation. For example, formulations for oral administration containing the composition of the present disclosure as an active ingredient may include tablets, troches, lozenges, aqueous or oily suspensions, prepared powders or granules, emulsions, hard or soft capsules, and syrups or elixirs. For formulation into dosage forms such as tablets and capsules, a binder such as lactose, saccharose, sorbitol, mannitol, starch, amylopectin, cellulose, or gelatin, an excipient such as dicalcium phosphate, a disintegrant such as corn starch or sweet potato starch, or a lubricating oil such as magnesium stearate, calcium stearate, sodium stearyl fumarate, or polyethylene glycol wax may be included. In the case of capsule formulation, in addition to the above-mentioned substances, a liquid carrier such as fatty oil may be further included.

Formulations for parenteral administration including the composition of the present disclosure or the inhibitor of CDK17 expression or activity as an active ingredient may include injectable forms such as subcutaneous injection, intravenous injection, or intramuscular injection, a suppository injection method, or an aerosol that is inhaled through the respiratory tract. To formulate the composition of the present disclosure into an injectable dosage form, a solution or suspension is prepared by mixing the composition of the present disclosure, a stabilizer or buffer, and water, and the solution or suspension is formulated for unit administration in ampoules or vials. To inject the composition of the present disclosure as a suppository, the composition of the present disclosure may be formulated as a composition for rectal administration such as a suppository or body enema containing a conventional suppository base such as cocoa butter or other glycerides. When the composition of the present disclosure is formulated for spraying such as an aerosol, the composition of the present disclosure may be blended with an additive such as a propellant so that a water-dispersed concentrate or wet powder is dispersed.

The composition of the present disclosure or the inhibitor of CDK17 expression or activity may be administered in a dose of 100 μg/kg to 500 μg/kg, without being limited thereto. The composition of the present disclosure may be administered in combination with a known therapeutic agent for fibrosis at a different time or at the same time, or a known method for treating fibrosis may be applied together. The composition may also be administered single or multiple. Taking all of the above factors into consideration, it is important to administer an amount that may obtain the maximum effect with a minimum amount without side effects, which may be easily determined by those skilled in the art.

In the present disclosure, the term "administration" refers to introducing the pharmaceutical composition of the present disclosure to an individual by any suitable method, and administration may be carried out through various routes, either oral or parenteral, as long as the composition may reach a target tissue.

The pharmaceutical composition may be appropriately administered to a subject according to a conventional method, an administration route, and dosage used in the art, depending on the purpose or necessity. Examples of the administration route include oral, parenteral, subcutaneous, intraperitoneal, intrapulmonary, and intranasal administration, and parenteral injection includes intramuscular, intravenous, intraarterial, intraperitoneal, or subcutaneous administration. In addition, an appropriate dosage and frequency of administration may be selected according to methods known in the art. The amount and frequency of administration of the pharmaceutical composition of the present disclosure may be appropriately determined in consideration of various factors such as the type of symptom to be treated, administration route, sex, health status, diet, age and weight of a subject, and the severity of a disease.

In the present disclosure, the term "pharmaceutically effective amount" means an amount sufficient to inhibit or alleviate increase in vascular permeability at a reasonable benefit/risk ratio applicable to medical use. An effective dose level may be determined in consideration of subject type, severity, age, sex, drug activity, sensitivity to drug, administration time, administration route, excretion rate, duration of treatment, factors including concurrent drugs, and other factors well known in the medical field.

In the present disclosure, the term "subject" refers to a subject, and includes animals such as horses, sheep, pigs, goats, camels, antelopes, and dogs, preferably mammals or humans, having related diseases whose symptoms may be alleviated by administration of the pharmaceutical composition according to the present disclosure.

Accordingly, the present disclosure includes a method of preventing or treating fibrosis including a step of administering an inhibitor of CDK17 expression or activity, or a composition including the inhibitor of CDK17 expression or activity to a subject.

The prophylactic or therapeutic method of the present disclosure includes administering the inhibitor of CDK17 expression or activity, or the composition of the present disclosure in a therapeutically effective amount. The therapeutically effective amount means an amount that enhances a fibrosis inhibitory effect. It is apparent to those skilled in the art that a suitable total daily amount may be determined by a treating physician within the scope of sound medical judgment. A specific therapeutically effective amount for a particular patient is preferably determined depending on the type and extent of a response to be achieved, whether other agents are used in some cases, the patient's age, weight, general health, sex and diet, administration time, route of administration, the secretion rate of a composition, a treatment period, and various factors well known in the medical field. Accordingly, the effective amount of the pharmaceutical composition suitable for the purpose of the present disclosure is preferably determined in consideration of the above factors. In addition, in some cases, a known therapeutic agent for a related disease may be administered in combination with the composition of the present disclosure to increase the therapeutic effect of the related disease.

In addition, the present disclosure relates to a health functional food for preventing or alleviating fibrosis including the inhibitor of CDK17 expression or activity as an active ingredient.

In addition to the inhibitor of CDK17 expression or activity, the health functional food of the present disclosure may further include an appropriate food supplement additive.

In the present disclosure, the term "food supplement additive" refers to a component that may be supplementally added to food, and is added to manufacture a health functional food of each formulation, and may be appropriately selected by those skilled in the art. Examples of food supplement additives include various nutrients, vitamins, minerals (electrolytes), synthetic flavoring agents, flavoring agents such as natural flavoring agents, coloring agents, fillers, pectic acid and salts thereof, alginic acid and salts thereof, organic acids, protective colloidal thickeners, pH adjusters, stabilizers, preservatives, glycerin, alcohols, and carbonation agents used in carbonated beverages, but the types of food supplement additives of the present disclosure are not limited to the above examples.

The food composition of the present disclosure may include a health functional food. In the present disclosure, the term "health functional food" refers to food manufactured and processed in the form of tablets, capsules, powders, granules, liquids, and pills using raw materials or ingredients useful for the human body. Here, the term "functionality" refers to obtaining useful effects for health purposes, such as regulating nutrients or physiological effects on the structure and function of the human body. The health functional food of the present disclosure may be manufactured by a method commonly used in the art, and raw materials and components commonly used in the art may be added during manufacturing. In addition, unlike general drugs, there is no side effect and excellent portability when taking a drug containing food as a raw material for a long period of time. Accordingly, the health functional food of the present disclosure may be taken as an adjuvant for enhancing the prevention or treatment effect of related diseases. The mixing amount of the active ingredient may be appropriately determined depending on the purpose of use (prophylactic, health, or therapeutic treatment). In general, in the production of food, the inhibitor of CDK17 expression or activity according to the present disclosure is added in an amount of 1 to 10% by weight, preferably 5 to 10% by weight based on the total weight of the composition. However, in the case of long-term intake for health and hygiene purposes or for health control, the amount may be reduced below the above range.

There is no particular limitation on the type of the food. Examples of foods to which the above substances may be added include meat, sausage, bread, chocolate, candies, snacks, confectionery, pizza, ramen, other noodles, gums, dairy products including ice cream, various soups, beverages, tea, drinks, alcoholic beverages, vitamin complexes, and the like, and includes all health foods in the ordinary sense.

The health food composition of the present disclosure may contain various flavoring agents or natural carbohydrates as additional ingredients, like conventional food. The above-mentioned natural carbohydrates include monosaccharides such as glucose and fructose, disaccharides such as maltose and sucrose, polysaccharides such as dextrin and cyclodextrin, and sugar alcohols such as xylitol, sorbitol, and erythritol. As the sweetener, natural sweeteners such as taumartin and *stevia* extract, synthetic sweeteners such as saccharin and aspartame, and the like may be used. In general, the proportion of the natural carbohydrate is about 0.01 to 0.04 g, preferably about 0.02 to 0.03 g per 100 g of the composition of the present disclosure.

BRIEF DESCRIPTION OF THE DRAWINGS

The above and other objects, features and other advantages of the present disclosure will be more clearly understood from the following detailed description taken in conjunction with the accompanying drawings, in which:

FIG. 1 is a graph showing the knockdown efficiency of CDK17 siRNAs in activated human hepatic stellate cells (hTERT-HSCs) as measured by RT-qPCR;

FIG. 2 is a graph showing a decrease in collagen-encoding hCOL1A1 mRNA levels by CDK17 siRNAs in hTERT-HSCs as measured by RT-qPCR;

FIG. 3 includes western blotting results showing a decrease in alpha-SMA protein levels by CDK17 siRNAs in hTERT-HSCs;

FIG. 4 is a graph showing a decrease in the viability of hTERT-HSCs by CDK17 siRNA treatment, and cell viability was evaluated by absorbance measured at 450 nm using a plate reader;

FIG. 5 is an RT-qPCR result showing the knockdown efficiency of CDK17 siRNAs in human renal tubular epithelial cells (HK-2 cells) in which fibrosis is induced by TGF-β treatment;

FIG. 6 is an RT-qPCR result showing a decrease in collagen-encoding hCOL1A1 mRNA levels by CDK17 siRNAs in HK-2 cells in which fibrosis is induced by TGF-β treatment;

FIG. 7 includes western blotting results showing a decrease in alpha-SMA protein levels by CDK17 siRNAs in HK-2 cells in which fibrosis is induced by TGF-β treatment;

FIG. 8 is a graph showing a decrease in the viability of HK-2 cells, by CDK17 siRNA treatment, in which fibrosis is induced by TGF-β treatment, and cell viability was evaluated by absorbance measured at 450 nm using a plate reader;

FIG. 9 is a graph showing the knockdown efficiency of CDK17 siRNA in human alveolar epithelial cells (A549 cells) in which fibrosis is induced by TGF-β treatment, as measured by RT-qPCR;

FIG. 10 is a RT-qPCR result showing a decrease in a collagen-encoding hCOL1A1 mRNA levels by CDK17 siRNAs in A549 cells in which fibrosis is induced by TGF-β treatment;

FIG. 11 includes western blotting results showing a decrease in alpha-SMA protein levels by CDK17 siRNAs in A549 cells in which fibrosis is induced by TGF-β treatment; and FIG. 12 is a graph showing a decrease in the viability of A549 cells, by CDK17 siRNA treatment, in which fibrosis is induced by TGF-β treatment, and cell viability was evaluated by absorbance measured at 450 nm using a plate reader.

DETAILED DESCRIPTION OF THE DISCLOSURE

The present disclosure will now be described more fully with reference to the accompanying drawings, in which exemplary embodiments of the disclosure are shown. The disclosure may, however, be embodied in many different forms and should not be construed as being limited to the embodiments set forth herein; rather, these embodiments are provided so that this disclosure will be thorough and complete, and will fully convey the concept of the disclosure to those skilled in the art. The present disclosure is defined only by the categories of the claims.

Example 1: Confirmation of the Efficacy of CDK17 Gene Knockdown in Treatment of Liver Fibrosis "Activated hepatic stellate cells" are key in liver fibrosis, and main strategies for treating liver fibrosis based on "activated hepatic stellate cells" include 1) decreasing the viability of "activated hepatic stellate cells", 2) decreasing the proliferation of "activated hepatic stellate cells", 3) decreasing the activity of "activated hepatic stellate cells" or converting "activated hepatic stellate cells" into "resting hepatic stellate cells", and 4) inhibiting collagen production by "activated hepatic stellate cells". Accordingly, based on the possibility of association between a CDK17 gene and the viability and proliferation of hTERT-HSCs, which are "activated hepatic stellate cells", as a strategy for treating liver fibrosis, it was confirmed whether CDK17 gene knockdown affected the viability, activity, and collagen production of hTERT-HSCs.

Specifically, experiments were conducted using three CDK17 siRNAs of different nucleotide sequences.

1) Construction of CDK17 siRNAs

Three different siRNAs for a human CDK17 gene [GenBank accession number: NM_001170464.4] were purchased from BIONEER, and nucleotide sequences of each CDK17 siRNA are as follows.

```
Human CDK17 siRNA #1:
                    (sense, SEQ ID NO: 1)
GUCCUCUUCACAGUGGAGU
and
                    (antisense, SEQ ID NO: 2)
ACUCCACUGUGAAGAGGAC Human CDK17 siRNA #2:
                    (sense, SEQ ID NO: 3)
CUAACAAACUGCUGUUCUU
and
                    (antisense, SEQ ID NO: 4)
AAGAACAGCAGUUUGUUAG Human CDK17 siRNA #3:
                    (sense, SEQ ID NO: 5)
CAGUACACAGGAUCUUUCA
and
                    (antisense, SEQ ID NO: 6)
UGAAAGAUCCUGUGUACUG
```

2) Evaluation of CDK17 Gene Knockdown Efficiency of CDK17 siRNAs

To evaluate the knockdown efficiency of each of three different CDK17 siRNAs, hTERT-HSCs were seeded on each well of a 24-well plate at a cell density of $2.0 \times 10^4$ cells/well. After 24 hours, hTERT-HSCs were subjected to mock treatment or transfected with a negative control siRNA (NC) or each CDK17 siRNA at a final concentration of 100 nM. After incubation for 2 days, RT-qPCR was performed to confirm whether each of the three different CDK17 siRNAs effectively reduced the level of CDK17 mRNA (FIG. 1). As a result, it was confirmed that each of the three different CDK17 siRNAs significantly and effectively reduced CDK17 gene expression.

3) Evaluation of hCOL1A1 Expression after CDK17 siRNA-Mediated CDK17 Gene Knockdown hTERT-HSCs were seeded on each well of a 24-well plate at a cell density of $2.0 \times 10^4$ cells/well. After 24 hours, hTERT-HSCs were subjected to mock treatment or transfected with a negative control siRNA (NC) or each of three different CDK17 siRNAs at a final concentration of 100 nM. After incubation for 2 days, RT-qPCR was performed to confirm whether each of the three different CDK17 siRNAs significantly and effectively reduced the mRNA level of human alpha-1 type I collagen (hCOL1A1) for collagen production (FIG. 2). As a result, CDK17 gene knockdown significantly reduced collagen production of "activated hepatic stellate cells", indicating that CDK17 gene knockdown is effective in treating liver fibrosis.

4) Evaluation of alpha-SMA expression after CDK17 siRNA-mediated CDK17 gene knockdown In treatment of liver fibrosis, it is important to inhibit the activity of "activated hepatic stellate cells". hTERT-HSCs were seeded on each well of a 24-well plate at a cell density of $2.0 \times 10^4$ cells/well. After 24 hours, hTERT-HSCs were subjected to mock treatment or transfected with a negative control siRNA (NC) or each of three different CDK17 siRNAs at a final concentration of 100 nM. After incubation for 2 days, western blotting was performed for an alpha-SMA protein indicating the degree of activation of hTERT-HSCs.

As a result, compared to mock treatment and the negative control siRNA, in the case of each CDK17 siRNA, the level of the alpha-SMA protein as an activity marker was significantly reduced in hTERT-HSCs (FIG. 3). These results show that CDK17 gene knockdown significantly reduces the activity of "activated hepatic stellate cells", indicating that CDK17 gene knockdown is effective in treating liver fibrosis.

5) Evaluation of the viability of hTERT-HSCs after CDK17 siRNA-mediated CDK17 gene knockdown Next, to investigate whether CDK17 gene knockdown affected the viability of "activated hepatic stellate cells", hTERT-HSCs were treated with each of the three different CDK17 siRNAs, and the viability thereof was checked. Specifically, hTERT-HSCs were seeded on each well of a 96-well plate in a cell density of $3.0 \times 10^3$ cells/well. After 24 hours, hTERT-HSCs were subjected to mock treatment or transfected with a negative control siRNA (NC) or each CDK17 siRNA at a final concentration of 100 nM. Then, for 5 days, 10 μl of an EZ-Cytox reagent was added to each well at a predetermined time, incubation was performed for 1 hour, and then absorbance was measured at 450 nm using a plate reader.

As a result, compared to mock treatment and NC, in the case of the three different CDK17 siRNAs, the viability of hTERT-HSCs was significantly reduced (FIG. 4). These results show that CDK17 gene knockdown significantly reduces the viability of "activated hepatic stellate cells", indicating that CDK17 gene knockdown is effective in treating liver fibrosis. [76]

Example 2: Confirmation of the efficacy of CDK17 gene knockdown in treatment of renal fibrosis Renal fibrosis is a phenomenon found basically in most chronic kidney diseases, and renal fibrosis occurs when epithelial cells are converted into myofibroblasts by epithelial-mesenchymal transition (EMT) and extracellular matrix is accumulated in tissues. Transforming growth factor beta (TGF-β) is known as a main factor that causes this process. Based on these facts, main strategies for treating renal fibrosis include 1) reducing the viability of "human renal tubular epithelial cells (HK-2 cells) in which fibrosis is induced by TGF-β treatment", 2) reducing the proliferation of "HK-2 cells in which fibrosis is induced by TGF-β treatment", 3) reducing the activity of "HK-2 cells in which fibrosis is induced by TGF-β treatment", and 4) inhibiting collagen production by "HK-2 cells in which fibrosis is induced by TGF-β treatment". Accordingly, based on the possibility of association between CDK17 gene and the viability and proliferation of "HK-2 cells in which fibrosis is induced by TGF-β treatment", as a strategy for treating renal fibrosis, it was confirmed whether CDK17 gene knockdown affected the viability, activity, and collagen production of "HK-2 cells in which fibrosis is induced by TGF-β treatment". Specifically, experiments were conducted using three CDK17 siRNAs of different nucleotide sequences.

1) Construction of CDK17 siRNAs

Three different siRNAs for human CDK17 gene [GenBank accession number: NM_001170464.4] were purchased from BIONEER, and nucleotide sequences of each CDK17 siRNA are as follows.

```
Human CDK17 siRNA #1:
                    (sense, SEQ ID NO: 1)
GUCCUCUUCACAGUGGAGU
and (antisense, SEQ ID NO: 2)
ACUCCACUGUGAAGAGGAC Human CDK17 siRNA #2:
                    (sense, SEQ ID NO: 3)
CUAACAAACUGCUGUUCUU
and (antisense, SEQ ID NO: 4)
AAGAACAGCAGUUUGUUAG Human CDK17 siRNA #3:
                    (sense, SEQ ID NO: 5)
CAGUACACAGGAUCUUUCA
and (antisense, SEQ ID NO: 6)
UGAAAGAUCCUGUGUACUG
```

2) Evaluation of CDK17 gene knockdown efficiency of CDK17 siRNAs

To evaluate the knockdown efficiency of each of the three different CDK17 siRNAs, HK-2 cells were seeded on each well of a 24-well plate at a cell density of $4.0 \times 10^4$ cells/well. After 24 hours, TGF-β was added to each well at a final concentration of 10 ng/ml, and at the same time, HK-2 cells were subjected to mock treatment or transfected with a negative control siRNA (NC) or each CDK17 siRNA at a final concentration of 100 nM. After incubation for 2 days, RT-qPCR was performed to confirm whether each of the three different CDK17 siRNAs effectively reduced the level of CDK17 mRNA (FIG. 5). As a result, it was confirmed that each of the three different CDK17 siRNA significantly and effectively reduced CDK17 gene expression.

3) Evaluation of hCOL1A1 expression after CDK17 siRNA-mediated CDK17 gene knockdown HK-2 cells were seeded on each well of a 24-well plate at a cell density of $4.0 \times 10^4$ cells/well. After 24 hours, TGF-β was added to each well at a final concentration of 10 ng/ml, and at the same time, HK-2 cells were subjected to mock treatment or transfected with a negative control siRNA (NC) or each of the three different CDK17 siRNAs at a final concentration of 100 nM. After incubation for 2 days, RT-qPCR was performed to confirm whether each of the three different CDK17 siRNAs significantly and effectively reduced the mRNA level of human alpha-1 type I collagen (hCOL1A1) for collagen production (FIG. 6). As a result, CDK17 gene knockdown significantly reduced collagen production by "HK-2 cells in which fibrosis is induced by TGF-β treatment", indicating that CDK17 gene knockdown is effective in treating renal fibrosis.

4) Evaluation of Alpha-SMA Expression after CDK17 siRNA-Mediated CDK17 Gene Knockdown In treating renal fibrosis, it is important to inhibit the activity of "HK-2 cells in which fibrosis is induced by TGF-β treatment". Specifically, HK-2 cells were seeded on each well of a 24-well plate at a cell density of $4.0 \times 10^4$ cells/well. After 24 hours, TGF-β was added to each well at a final concentration of 10 ng/ml, and at the same time, HK-2 cells were subjected to mock treatment or transfected with a negative control siRNA (NC) or each of three different CDK17 siRNAs at a final concentration of 100 nM. After incubation for 2 days, western blotting was performed for an alpha-SMA protein indicating the degree of activation of "HK-2 cells in which fibrosis is induced by TGF-β treatment".

As a result, compared to mock treatment and the negative control siRNA, in the case of each CDK17 siRNA, the level of the alpha-SMA protein as an activity marker was significantly reduced in "HK-2 cells in which fibrosis was induced by TGF-β treatment" (FIG. 7). These results show that CDK17 gene knockdown significantly reduces the activity of "HK-2 cells in which fibrosis is induced by TGF-β treatment", indicating that CDK17 gene knockdown is effective in treating renal fibrosis.

5) Evaluation of the Viability of "HK-2 Cells in which Fibrosis is Induced by TGF-r3 Treatment" after CDK17 siRNA-Mediated CDK17 Gene Knockdown Next, to investigate whether CDK17 gene knockdown affected the viability of "HK-2 cells in which fibrosis was induced by TGF-β treatment", "HK-2 cells in which fibrosis was induced by TGF-β treatment" were treated with each of the three different CDK17 siRNAs, and the viability thereof was evaluated. Specifically, HK-2 cells were seeded on each well of a 96-well plate at a cell density of $5.0 \times 10^3$ cells/well. After 24 hours, TGF-β was added to each well at a final concentration of 10 ng/ml, and at the same time, HK-2 cells were subjected to mock treatment or transfected with a negative control siRNA (NC) or each CDK17 siRNA at a final concentration of 100 nM. Then, for 5 days, 10 µl of an EZ-Cytox reagent was added to each well at a predetermined time, incubation was performed for 1 hour, and then absorbance was measured at 450 nm using a plate reader.

As a result, compared to mock treatment and NC, in the case of the three different CDK17 siRNAs, the viability of "HK-2 cells in which fibrosis was induced by TGF-β treatment" was significantly reduced (FIG. 8). These results show that CDK17 gene knockdown significantly reduces the viability of "HK-2 cells in which fibrosis is induced by TGF-β treatment", indicating that CDK17 gene knockdown is effective in treating renal fibrosis.

Example 3: Confirmation of the Efficacy of CDK17 Gene Knockdown in Treatment of Lung Fibrosis Lung fibrosis is a phenomenon found basically in most chronic lung diseases, and lung fibrosis occurs when epithelial cells are converted into myofibroblasts by epithelial-mesenchymal transition (EMT) and extracellular matrix is accumulated in tissues. Transforming growth factor beta (TGF-β) is known as a main factor that causes this process. Based on these facts, main strategies for treating lung fibrosis include 1) reducing the viability of "human alveolar epithelial cells (A549 cells) in which fibrosis is induced by TGF-β treatment", 2) reducing the proliferation of "A549 cells in which fibrosis is induced by TGF-β treatment", 3) reducing the activity of "A549 cells in which fibrosis is induced by TGF-β treatment", and 4) inhibiting collagen production by "A549 cells in which fibrosis is induced by TGF-β treatment". Based on the possibility of association between CDK17 gene and the viability and proliferation of "A549 cells in which fibrosis was induced by TGF-β treatment", as a strategy for treating lung fibrosis, it was confirmed whether CDK17 gene knockdown affected the viability, activity, and collagen production of "A549 cells in which fibrosis was induced by TGF-β treatment". Specifically, experiments were conducted using three CDK17 siRNAs of different nucleotide sequences. [96] 1) Construction of CDK17 siRNAs [97] Three different siRNAs for human CDK17 gene [GenBank accession number: NM_001170464.4] were purchased from BIONEER, and nucleotide sequences of each CDK17 siRNA are as follows.

```
Human CDK17 siRNA #1:
                     (sense, SEQ ID NO: 1)
GUCCUCUUCACAGUGGAGU
and (antisense, SEQ ID NO: 2)
ACUCCACUGUGAAGAGGAC Human CDK17 siRNA #2:
                     (sense, SEQ ID NO: 3)
CUAACAAACUGCUGUUCUU
and (antisense, SEQ ID NO: 4)
AAGAACAGCAGUUUGUUAG Human CDK17 siRNA #3:
                     (sense, SEQ ID NO: 5)
CAGUACACAGGAUCUUUCA
and (antisense, SEQ ID NO: 6)
UGAAAGAUCCUGUGUACUG
```

2) Evaluation of CDK17 Gene Knockdown Efficiency of CDK17 siRNAs

To evaluate the knockdown efficiency of each of the three different CDK17 siRNAs, A549 cells were seeded on each well of a 24-well plate at a cell density of $4.0 \times 10^4$ cells/well. After 24 hours, TGF-β was added to each well at a final concentration of 10 ng/ml, and at the same time, A549 cells were subjected to mock treatment or transfected with a negative control siRNA (NC) or each CDK17 siRNA at a final concentration of 100 nM. After incubation for 2 days, RT-qPCR was performed to confirm whether each of the three different CDK17 siRNAs effectively reduced the level of CDK17 mRNA (FIG. 9). As a result, each of the three different CDK17 siRNAs significantly and effectively reduced CDK17 gene expression.

3) Evaluation of hCOL1A1 Expression after CDK17 siRNA-Mediated CDK17 Gene Knockdown A549 cells were seeded on each well of a 24-well plate at a cell density of $4.0 \times 10^4$ cells/well. After 24 hours, TGF-β was added to each well at a final concentration of 10 ng/ml, and at the same time, A549 cells were subjected to mock treatment or transfected with a negative control siRNA (NC) or each of the three different CDK17 siRNAs at a final concentration of 100 nM. After incubation for 2 days, RT-qPCR was performed to confirm whether each of the three different CDK17 siRNAs significantly and effectively reduced the mRNA level of human alpha-1 type I collagen (hCOL1A1) for collagen production (FIG. 10). As a result, CDK17 gene knockdown significantly inhibited collagen production by "A549 cells in which fibrosis was induced by TGF-β treatment", indicating that CDK17 gene knockdown is effective in treating lung fibrosis.

4) Evaluation of Alpha-SMA Expression after CDK17 siRNA-Mediated CDK17 Gene Knockdown In treating lung fibrosis, it is important to inhibit the activity of "A549 cells in which fibrosis is induced by TGF-β treatment". Specifically, A549 cells were seeded on each well of a 24-well plate at a cell density of $4.0 \times 10^4$ cells/well. After 24 hours, TGF-β was added to each well at a final concentration of 10 ng/ml, and at the same time, A549 cells were subjected to mock treatment or transfected with a negative control siRNA (NC) or each of three different CDK17 siRNAs at a final concentration of 100 nM. After incubation for 2 days, western blotting was performed for an alpha-SMA protein indicating the degree of activation of "A549 cells in which fibrosis was induced by TGF-β treatment".

As a result, compared to mock treatment and the negative control siRNA, in the case of each CDK17 siRNA, the level of the alpha-SMA protein as an activity marker was significantly reduced in "A549 cells in which fibrosis was induced by TGF-β treatment" (FIG. 11). These results show that CDK17 gene knockdown significantly reduces the activity of "A549 cells in which fibrosis is induced by TGF-β treatment", indicating that CDK17 gene knockdown is effective in treating lung fibrosis.

5) Evaluation of the viability of "A549 Cells in which Fibrosis is Induced by TGF-r3 Treatment" after CDK17 siRNA-Mediated CDK17 Gene Knockdown Next, to investigate whether CDK17 gene knockdown affected the viability of "A549 cells in which fibrosis was induced by TGF-β treatment", "A549 cells in which fibrosis was induced by TGF-β treatment" were treated with each of the three different CDK17 siRNAs, and the viability thereof was evaluated. Specifically, A549 cells were seeded on each well of a 96-well plate at a cell density of $5.0 \times 10^3$ cells/well. After 24 hours, TGF-β was added to each well at a final concentration of 10 ng/ml, and at the same time, A549 cells were subjected to mock treatment or transfected with a negative control siRNA (NC) or each CDK17 siRNA at a final concentration of 100 nM. Then, for 5 days, 10 μl of an EZ-Cytox reagent was added to each well at a predetermined time, incubation was performed for 1 hour, and then absorbance was measured at 450 nm using a plate reader.

As a result, compared to mock treatment and NC, in the case of each of the three different CDK17 siRNAs, the viability of "A549 cells in which fibrosis was induced by TGF-β treatment" was significantly reduced (FIG. 12). These results show that CDK17 gene knockdown significantly reduces the viability of "A549 cells in which fibrosis is induced by TGF-β treatment", indicating that CDK17 gene knockdown is effective in treating lung fibrosis.

In activated human hepatic stellate cells (liver fibrosis cell model), human renal tubular epithelial cells (renal fibrosis cell model) in which fibrosis is induced by TGF-β treatment, and human alveolar epithelial cells (lung fibrosis cell model) in which fibrosis is induced by TGF-r3 treatment, cell activity and viability can be significantly reduced by CDK17 gene knockdown. In addition, in activated human hepatic stellate cells, human renal tubular epithelial cells in which fibrosis is induced by TGF-β treatment, and human alveolar epithelial cells in which fibrosis is induced by TGF-β treatment, collagen production can be significantly reduced by CDK17 gene knockdown. These findings confirm that CDK17 gene knockdown is effective in treatment of fibrosis.

According to the present disclosure, an inhibitor of CDK17 expression or activity can be used to prevent or treat fibrosis.

The aforementioned description of the present disclosure is provided by way of example and those skilled in the art will understand that the present disclosure can be easily changed or modified into other specified forms without change or modification of the technical spirit or essential characteristics of the present disclosure. Therefore, it should be understood that the aforementioned examples are only provided by way of example and not provided to limit the present disclosure. It should be understood that the scope of the present disclosure is defined by the following claims and the disclosure is to cover all modifications, equivalents, and alternatives falling within the spirit and scope of the disclosure as defined by the claims.

What is claimed is:

1. A method of preventing or treating fibrosis, comprising administering to a subject in need thereof a therapeutically effective amount of a CDK17 ribonucleic acid-based inhibitor, or a composition comprising the CDK17 ribonucleic acid-based inhibitor.

2. The method according to claim 1, wherein the ribonucleic acid is siRNA.

3. The method according to claim 1, wherein the fibrosis occurs in lungs, kidneys, a liver, a heart, a brain, blood vessels, joints, intestines, skin, soft tissues, bone marrow, a penis, a peritoneum, muscles, a spine, testes, ovaries, breasts, a thyroid, tympanic membranes, a pancreas, a gallbladder, a bladder, or a prostate.

4. The method according to claim 1, wherein the composition further comprises a pharmaceutically acceptable carrier.

* * * * *